(12) United States Patent
Paulus et al.

(10) Patent No.: US 6,458,991 B1
(45) Date of Patent: Oct. 1, 2002

(54) PREPARATION OF (METH)ACRYLATES

(75) Inventors: Wolfgang Paulus, Ober-Olm; Wolfgang Reich, Maxdorf; Erich Beck, Ladenburg; Thomas Jaworek, Kallstadt; Rainer Königer, Freinsheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/592,736

(22) Filed: Jun. 13, 2000

(30) Foreign Application Priority Data

Jun. 25, 1999 (DE) .......................................... 199 29 258

(51) Int. Cl.⁷ .............................................. C07C 69/52
(52) U.S. Cl. ...................... 560/224; 560/205
(58) Field of Search ................... 560/224, 205

(56) References Cited

U.S. PATENT DOCUMENTS

| | | | |
|---|---|---|---|
| 3,912,626 A | * | 10/1975 | Ely et al. |
| 4,217,209 A | * | 8/1980 | Steffan et al. |
| 5,096,938 A | * | 3/1992 | Beck et al. |
| 5,198,574 A | | 3/1993 | Ritter et al. |
| 5,350,877 A | * | 9/1994 | Ritter et al. |
| 5,648,518 A | | 7/1997 | Ritter et al. |

FOREIGN PATENT DOCUMENTS

| | | |
|---|---|---|
| DE | 3 316 5 93 | 11/1984 |
| DE | 4 019 7 88 | 1/1992 |
| DE | 4 430 0 86 | 2/1996 |

OTHER PUBLICATIONS

Baldwin et al; Chemistry and Industry, 1970, No. 18, pp. 595–597.*
Oke R.A.; Wragg R.T., "Chem. and Ind." 18 (1970), 597.*

* cited by examiner

*Primary Examiner*—Gary Geist
*Assistant Examiner*—Farhad Forohar
(74) *Attorney, Agent, or Firm*—Oblon, Spivak, McClelland, Maier & Neustadt, P.C.

(57) ABSTRACT

Compounds having alcoholic hydroxyl groups are esterified with acrylic or methacrylic acid in the presence of copper(II) salts or mixtures thereof as polymerization inhibitors and in the presence of a hydrocarbon as a water-entraining agent with removal of the water of reaction at from 90 to 150° C. After the esterification, the copper salt is precipitated as copper sulfide and is separated off from the ester. The light-color (meth)acrylates resulting in the high yields are particularly suitable for coatings containing colored pigment on substrates such as wood, paper, mineral building materials, plastics or metal.

10 Claims, No Drawings

PREPARATION OF (METH)ACRYLATES

The present invention relates to an improved process for the preparation of light esters of acrylic acid and/or methacrylic acid from alcohols which may be alkoxylated, in the presence of an acidic esterification catalyst and of a copper compound as polymerization inhibitor.

Radiation-curable binders based on monomeric and oligomeric acrylates of alcohols have become increasingly interesting commercially as coating resins and other coating materials, owing to their solvent-free and easy processability. There is therefore a continuing need for improved preparations of the (meth)acrylates of in particular polyhydric alcohols, their alkoxylated derivatives, polyether polyols or polyester polyols, as shown by the numerous patent applications in this area. Thus, reference may be made to the German Patent Applications DE-A 3316593, DE-A 3704098, DE-A 3843854, DE-A 3843930, DE-A 3843938, DE-A 4019788 and DE-A 4430086 as prior art.

The esterification of alcohols and in particular polyols with methacrylic acid and preferably acrylic acid have been described in many publications. Apart from a preparation by transesterification, the preferred method of preparing (meth) acrylates is the direct esterification of alcohols or polyols with acrylic acid or methacrylic acid in the presence of an esterification catalyst and of a solvent which forms an azeotropic mixture with water and serves as a water-entraining agent. To accelerate the esterification reaction, it is desirable to choose reaction temperatures of more than 90° C. and in particular more than 100° C., also for the subsequent rapid distillative removal of the acrylic acid and/or methacrylic acid generally used in excess. High reaction temperatures require the use of larger amounts of polymerization inhibitors in order to achieve good yields of the esterification products and for effectively suppressing the polymerization of (meth)acrylic acid and esters thereof. Since said polymerization inhibitors remain in the reaction product even after the excess (meth)acrylic acid has been distilled off, the concomitant use of polymerization inhibitors imparting a strong color, such as copper salts, phenothiazine, hydroquinone and derivatives thereof, is not expedient for the preparation of light esterification products. They generally lead to dark end products. Although the use, known per se, of a copper salt as a polymerization inhibitor in the preparation of (meth)acrylates permits high esterification temperatures, it was then necessary, for the preparation of light products, to wash out the copper salt in a wash step, which is time-consuming, reduces the ester yield, increases the requirement of solvents as a water-entraining agent, which have to be distilled off again, and furthermore leads to a high level of pollution of waste water.

It is an object of the present invention to provide a simple process for the preparation of (meth)acrylates which gives light esterification products in good yield.

We have found that this object is achieved by a process for the preparation of (meth)acrylates by esterification of acrylic acid/and or methacrylic acid with at least one compound having one or more alcoholic hydroxyl groups at an esterification temperature of from 90 to 150° C. in the presence of an acidic esterification catalyst and of a polymerization inhibitor with the addition of a hydrocarbon having a boiling point of from 40 to 120° C. as a water-entraining agent, the water-entraining agent and excess (meth)acrylic acid being distilled off at from 90 to 150° C. at atmospheric pressure or reduced pressure after the esterification and, if required, the acidic product obtained after the distillation being neutralized with at least one basic inorganic compound, wherein the polymerization inhibitor used is a copper(II) salt, a copper(I) salt or a mixture thereof, the copper being precipitated as copper sulfide after the esterification and being separated off.

The novel process thus combines the advantages of using a high temperature for a more rapid esterification and rapid distillative removal of the excess of (meth)acrylic acid with the advantage of a low requirement of solvent as water-entraining agent, with the advantage of effective removal of the copper salt as polymerized inhibitor without the use of a wash step and with the advantage of the preparation of light end products (iodine number$\leqq$5, preferably$\leqq$3, in particular$\leqq$2) in good yield.

Acids used for the esterification reaction are methacrylic acid, acrylic acid or mixtures thereof, the preferred acid being acrylic acid.

Suitable compounds having one or more alcoholic hydroxyl groups, in addition to alcohols, such as lauryl alcohol or 2-ethylhexyl alcohol, are in particular polyols having 2 to 6 alcoholic hydroxyl groups. Examples of compounds having alcoholic hydroxyl groups are alcohols having 2 to 20, preferably 2 to 10, carbon atoms, such as ethylene glycol, propylene glycol, 1,2-, 1,3- and 1,4-butanediol, neopentylglycoi, di- and triethylene glycol, di- and tripropylene glycol, 1,5-pentanediol, 1,6-hexanediol, glycerol, trimethylolethane, trimethylolpropane, ditrimethyloipropane, sorbitol, pentaerythritol or dipentaerythritol. Very suitable components having alcoholic hydroxyl groups are also alkoxylation products such as alcohols and in particular ethoxylated and/or propoxylated polyhydric alcohols such as oxyethylated trimethylolpropane, ethoxylated and/or propoxylated pentaerythritol. In general, such alkoxylated alcohols contain 1 to 20 and preferably 1 to 10 alkoxy groups in the polyol molecule. In addition to polyether polyols, other polyols used may be polyester polyols, ether-modified polyesterpblyols, polyepoxy resins having a plurality of aliphatic hydroxyl groups or corresponding polyurethanes. Liquid to viscous low molecular weight and oligomeric compounds having alcoholic hydroxyl groups are particularly suitable for the esterification reaction.

For the esterification reaction, the components containing acid and hydroxyl groups are used in particular in amounts of from 1 to 1.5 mol of acid per hydroxyl group of the mono- or polyol component. However, the amount of acid can also be correspondingly reduced if only some of the hydroxyl groups of polyols are to be converted into acrylates and/or methacrylates.

Suitable acidic esterification catalysts are strong organic or inorganic acids, which are generally used in amounts from 0.1 to 5% by weight, based on the sum of the amounts of alcohol and of (meth)acrylic acid component. Preferred acidic esterification catalysts are sulfuric acid, p-toluenesulfonic acid, methanesulfonic acid and strongly acidic ion exchangers.

The esterification can be carried out at atmospheric, subatmospheric or reduced pressure.

Polymerization inhibitors used in the novel process for the esterification reaction and for distilling off the excess (meth)acrylic acid are copper(II) salts, in particular copper (II)chloride, copper(II)nitrate or copper(II) sulfate, or a mixture of a copper(II) salt and a copper(I) salt. The amount of inhibitor should be sufficient for effective inhibition of the polymerization of the (meth)acrylic acid and esters thereof during the esterification reaction and the subsequent distilling off of the excess (meth)acrylic acid. It is preferable to use the copper salts in an amount of at least 0.02 and in particular from 0.2 to 0.6% by weight, based on the resulting amount of (meth)acrylate.

It has proven advantageous also to add to the esterification mixture, before the esterification reaction, hypophosphorous acid ($H_3PO_2$), triphenyl phosphite or an organophosphonic acid, such as 1-hydroxyethane-1,1-diphosphonic acid, as a color stabilizer in an amount of 0.01 to 3% by weight, based on the resulting amount of ester. Further conventional polymerization inhibitors, color stabilizers, etc., such as hydroquinone compounds, e.g. hydroquinones monomethyl ether, can be added to the batch in conventional amounts in the novel process after the excess (meth)acrylic acid has been distilled off, without substantially impairing the quality of the products.

The esterification of the compound(s) having alcoholic hydroxyl groups or polyols with (meth)acrylic acid is carried out at from 90 to 150° C., in particular from 95 to 140° C., preferably from 100 to 130° C., particularly preferably from 110 to 120° C., while stirring at atmospheric, superatmospheric or reduced pressure in the presence of a suitable hydrocarbon as a water-entraining agent for removing the water of reaction obtained in the esterification. Suitable hydrocarbons are aliphatic, cycloaliphatic or aromatic hydrocarbons which form an azeotrope with the water of reaction. They should preferably have a boiling point in the boiling range of from 60 to 150° C., preferably from 70 to 140° C. Examples of suitable hydrocarbons as water-entraining agents are n-heptane, cyclohexane, methylcyclohexane, benzene, toluene, xylene isomers, special naphthas and commercial hydrocarbon mixtures having the stated boiling points or boiling ranges. An advantage of the novel process is that only relatively small amounts of water-entraining agents are required. In general, they are used in an amount of from 0 to 35, in particular from 1 to 20, preferably from 2 to 10, % by weight, based on the mixture of (meth)acrylic acid and hydroxyl compound. The resulting water or reaction is removed during the esterification, with the result that the end of the esterification reaction is also detectable.

For the esterification reaction and the distilling off the excess (meth)acrylic acid, it has proven advantageous to flush the reactor with an inert gas/air mixture having an oxygen content from 1 to 20% by volume (lean air) or to bubble said mixture through in finely divided form, the gas stream preferably being bubbled through the reaction mixture and/or being passed through the reactor above the reaction mixture. The gas stream comprising lean air is used for removing from the reactor water of reaction formed during the esterification. During the esterification, the gas stream is limited so that, apart from the water of reaction, it removes very little (meth)acrylic acid, hydroxyl compound or (meth)acrylate from the reactor.

At the end of the esterification, in which a degree of esterification of at least 85 in particular from 90 to 95% is to be achieved, the hydrocarbon and then the excess (meth) acrylic acid are distilled off at from 90 to 150° C., in particular from 95 to 140° C., preferably from 100 to 130° C. and particularly preferably from 110 to 120° C., reduced pressure, in particular from 10 to 150, preferably from 30 to 80 mbar advantageously being employed and lean air expediently being used when reduced pressure is established.

The reaction product resulting after the distillation is acidic since it contains the acidic esterification catalyst and may also contain small amounts of (meth)acrylic acid. The product is therefore preferably neutralized. This is expediently carried out after cooling to about 20 to 100° C. The neutralization can be effected under wet conditions using aqueous basic solutions, such as sodium hydroxide solution or potassium hydroxide solution or aqueous sodium carbonate solutions. However, the acidic reaction product can also be subjected to dry neutralization i.e. dry neutralizing agents insoluble in the (meth)acrylate, such as hydroxides, oxides or carbonates of alkali metals, or alkaline earth metals and/or of aluminum, are added to it. Resulting water of neutralization can then be removed, for example, by applying reduced pressure.

According to the novel process, the copper salt still present as inhibitor is precipitated as copper sulfide and separated off. The term "after the esterification" is to be understood as meaning any time in the course of the further working up after the end of the reaction. The precipitation can be effected in particular after the excess (meth)acrylic acid has been distilled off or preferably after complete or partial neutralization of the acidic reaction product. The precipitation can also be carried out simultaneously with the neutralization.

The precipitation is carried out by adding an alkali metal sulfide or ammonium sulfide or an alkali metal hydrogen sulfide or ammonium hydrogen sulfide. The sulfide may be added in solid form, for example as a powder, or as the very highly concentrated aqueous or aqueous alcoholic solution. The copper sulfide formed is then removed in a conventional manner in the course of the subsequent process steps, for example, before the neutralization, after the partial neutralization or preferably after complete neutralization, for example by filtration with the aid of a pressure filter. Experiments with the aim of separating off the copper salt by means of strong complexing agents, such as Trilon®grades (ethylenediaminetetraacetic acid) or polyvinylpyrrolidone, were unsuccessful. A high copper content remained and led to a blue or green color on addition of amine. Example 1 below shows that this also occurs on adding aqueous salt solutions, such as solutions of sodium sulfite, sodium sulfate, sodium phosphate or sodium carbonate, and even in the case of sodium sulfide, when it has been added in too small an amount. If required, other salts may also be added. In order to remove the copper to a sufficient extent, addition of sodium sulfide in at least an equimolar amount, in particular in from 1 to 3 times the molar amount, based on the copper salt present, as required. The product sometimes still has a faint odor of hydrogen sulfide after precipitation of the copper salt as copper sulfide and removal thereof by filtration. If this is the case, deodorization of the end product is possible. This can be effected, for example, by passing lean air through the product heated to about 60 to 95° C. at a reduced pressure of from 10 to 200 mbar until an odor of hydrogen sulfide can no longer be detected. At the same time, the additional water is distilled off.

The inventive process is suitable for the industrial production of acrylate monomers, reactive thinners, polyether acrylates and polyester acrylates. The products prepared according to the invention are suitable in particular for uses which require light products, such as coatings containing color pigment on substrates such as wood, paper, plastics, mineral building materials, metals and coated metals.

The examples and comparative experiments which follow illustrate, but do not limit, the inventive process. Unless expressly stated otherwise, parts and percentages are by weight.

EXAMPLE 1

622.2 g of an ethoxylated pentaerythritol which contained on average 5 ethoxy groups-per pentaerythritol molecule (PP50), 604.36 g of acrylic acid, 0.6 g of hypophosphorous acid, 0.2 g of copper (II) chloride, 30.0 g of cyclohexane and 6.15 g of methanesulfonic acid were mixed and were esterified by heating to an external reactor temperature of 130° C. for 4 hours whilst stirring and bubbling through lean air, 115 ml of water being removed. After removal of the cyclohexane, the excess acrylic acid was distilled off at 130° C. and 40 mbar from the resulting batch having an acid number of 62 mg KOH/g, while bubbling through lean air. After distillation for 1 hour, the batch had an acid number of 10 mg KOH/g. The acid-containing PP50 acrylate thus obtained was cooled to 80° C. and then neutralized with 20 g of CaO (which corresponds to 2 g of CaO per 100 g of PP50 acrylate). Attempts were then made in various experiments to precipitate the copper (II) chloride contained in the batch in an amount of 0.02% of copper salt in each case by adding various 25% strength aqueous salt solutions. The experiments were carried out as shown in Table 1.

TABLE 1

Experiments on the precipitation of the copper (II) chloride

| Precipitating agent | Amount (%) | Green color an addition of 6% of diethylamine | Crosslinking in 1 week with light + room temperature |
| --- | --- | --- | --- |
| Na$_2$SO$_3$ | 0.02 | yes | yes |
| Na$_2$SO$_4$ | 0.02 | yes | yes |
| Na$_3$PO$_4$ | 0.02 | yes | yes |
| Na$_2$CO$_3$ | 0.02 | yes | yes |
| Seitz Ultra* | 0.02 | yes | yes |
| Sokalan CP5** | 0.02 | yes | yes |
| Na$_2$S | 0.01 | yes | yes |
| Na$_2$S | 0.015 | yes | yes |
| Na$_2$S | 0.02 | no | no |
| Na$_2$S | 0.03 | no | no |
| Na$_2$S | 0.04 | no | no |
| Na$_2$S | 0.06 | no | no |

*Seitz Ultra: Sheet silicate
**Sokalan CP5: Acrylic acid copolymer

As shown in Table 1, sufficient precipitation of the copper salt could be achieved only with Na$_2$S in an amount of at least 0.02% (based on the acrylate). These products were the only ones which were still not crosslinked on storage in light at room temperature after about 2 weeks.

EXAMPLE 2

A mixture of the starting materials stated in Example 1 was esterified at an external temperature of 130° C. while stirring for 4 hours, 118 ml of water being removed. After removal of the cyclohexane, the excess acrylic acid was distilled off at an external temperature of 130° C. and at 40 mbar from the resulting batch having an acid number of 57 mg KOH/g. After distillation for 1.5 hours, the acid-containing batch (acid-number 5.7 mg KOH/g) of the PP50 acrylate was neutralized with 11.4 g of CaO. The copper was precipitated as copper sulfide by adding 0.02% of Na$_2$S (as 25% strength aqueous solution) and was filtered off from the PP50 acrylate. The filtered PP50 acrylate was then deodorized at 95° C. and from 60 to 80 mbar by passing through lean air until an odor of hydrogen sulfide was no longer obtained. The resulting product had an iodine color number of less than 2 and a water content of 0.05%.

EXAMPLE 3

A mixture of 556.32 g of ethoxylated trimethylolpropane (TMP), which contained on average 3 ethoxy groups per molecule of trimethylolpropane (TP30), 475.2 g of acrylic acid, 0.5 g of hypophosphorous acid, 0.18 g of copper(II) chloride, 30.0 g of cyclohexane and 4.4 g of methanesulfonic acid was esterified for 5 hours at 130° C., 90 ml of water being removed. After removal of the cyclohexane, excess acrylic acid was distilled off at 130° C. and 40 mbar in the course of 1.5 hours. The resulting TP30 acrylate having an acid number of 5.7 mg KOH/g was cooled to 80° C. and neutralized with 11.4 g of CaO. Thereafter, the copper was precipitated as copper sulfide by adding 0.025% of sodium sulfide (as a 25% strength aqueous solution) and was filtered off from the TP30 acrylate. The filtered TP30 acrylate was then deodorized as stated in Example 2 until an odor of hydrogen sulfide was no longer obtained. The resulting acrylate had an iodine color number of 1–2 and a water content of less than 0.05%.

EXAMPLE 4

529.24 g of propoxylated trimethylolpropane (TMP), which contained on average 3 propoxy groups per molecule of TMP (TS30), 432 g of acrylic acid, 0.48 g of hypophosphorous acid, 0.16 g of copper (II) chloride, 30.0 g of cyclohexane and 4.0g of methanesulfonic acid were mixed and were esterified at an external temperature of 130° C. while stirring for 4 hours, 85 ml of water of reaction being removed. After removal of the cyclohexane, acrylic acid was distilled off in the course of 1.5 hours at an external temperature of 130° C. and at 40 mbar. The reaction product obtained had an acid number of 6 mg KOH/g and was cooled to 80° C. and then neutralized with 11.4 g of calcium oxide. The copper salt was precipitated as copper sulfide by adding 0.05% of sodium sulfide (as a 25% strength aqueous solution) and the TS30 acrylate was filtered. Deodorization of the product, which had an iodine color number of 1–2 and a water content of less than 0.05%, was not required.

EXAMPLE 5

A mixture of 472.0 g of 1,6-hexanediol, 691.2 g of acrylic acid, 0.18 g of copper (II) chloride, 0.54 g of hypophosphorous acid, 5.51 g of methanesulfonic acid and 80.0 g of cyclohexane was esterified by heating to an external temperature of 130° C. (internal temperature 97–108° C.) while stirring. After 4 hours, 158 ml of water had been removed and the esterification was virtually complete. The cyclohexane and the excess acrylic acid were then distilled off in the course of 1.5 hours at 105° C. at a reduced pressure of from 60 to 80 mbar established while bubbling 15 in lean air. The resulting intermediate had an acid number of 5.2 mg KOH/g and was stabilized with 0.1% of methylethylhydroquinone. The copper salt was precipitated as copper sulfide by adding an aqueous sodium sulfide solution (0.27 g of sodium sulfide in 2 g of water) and the 1,6-hexanediol acrylate was brought to a pH of 7–8 with 10% strength sodium hydroxide solution. The water present in the batch was then distilled off in the course of 1 hour at 105° C., and the product was filtered off. A light product having an iodine color of less than 2 and water content of 0.05% resulted.

EXAMPLE 6

The procedure was as in Example 5, except that the acrylic acid and the water were each distilled off at 95° C. The product quality 30 of the end product corresponded to the product prepared according to Example 5.

EXAMPLE 7

The procedure was as in Example 5, except that 1.5 times the amount of methanesulfonic acid was used as the esterification catalyst. The acid number of the intermediate after the acrylic acid had been distilled off was 8.2 mg KOH/g. Correspondingly more sodium hydroxide was used for the neutralization.

EXAMPLE 8

The procedure was as in Example 5, except that a mixture of 622.2 g of an ethoxylated pentaerythritol, which contained on average 5 ethoxy groups per molecule of pentaerythritol, 604.4 g of acrylic acid, 0.2 g of copper(II) chloride, 0.6 g of hypophosphorous acid, 6.2 g of methanesulfonic acid and 80.0 g of cyclohexane was used for the esterification. The esterification and the subsequent working up were carried out according to Example 5. The light end product had an iodine color number of 1–2 and a water content of less than 0.05%.

We claim:

1. A process for the preparation of (meth)acrylates, comprising esterification of acrylic acid and/or methacrylic acid with at least one compound which has at least one alcoholic hydroxyl group at from 90 to 150° C. in the presence of an acidic esterification catalyst and of a polymerization inhibitor with the addition of a hydrocarbon having a boiling point of from 60 to 140° C. as a water-entraining agent;

distilling off the water-entraining agent and excess (meth) acrylic acid at from 90 to 150° C. at atmospheric pressure or reduced pressure after the esterification; and, otpionally, neutralizing the product obtained after the distillation with at least one basic inorganic compound, wherein the polymerization inhibitor used is a copper (II) salt or a mixture of a copper(II) salt and a copper(I) salt, which is precipitated as copper sulfide after the esterification and is separated off.

2. A process as claimed in claim 1, the catalyst used being copper(II) chloride.

3. A process as claimed in claim 1, the catalyst being precipitated by adding an alkali metal sulfide or alkali metal hydrogen sulfide.

4. A process as claimed in claim 3, the alkali metal sulfide or alkali metal hydrogen sulfide being added in from 1 to 3 times the equimolar amount.

5. A process as claimed in claim 1, wherein the compound to be esterified and having alcoholic hydroxyl groups is an oxalkylation product of an aliphatic polyhydric alcohol.

6. A process as claimed in claim 1, wherein the resulting water of reaction is removed during the esterification.

7. A process as claimed in claim 1, wherein the acidic product obtained after the water-entraining agent and excess (meth)acrylic acid have been distilled off is neutralized with at least one basic inorganic compound insoluble in the (meth)acrylate.

8. A process as claimed in claim 1, wherein the acidic product obtained after the water-entraining agent and excess (meth)acrylic acid have been distilled off is neutralized in the dry state with oxides, hydroxides and/or carbonates of an alkali metal, or an alkaline earth metal and/or of aluminum.

9. A process as claimed in claim 1, wherein an inert gas/air mixture having an oxygen content of from 1 to 20 percent by volume is passed through the reaction mixture and/or through the reactor above said reaction mixture during the esterification and/or while excess (meth)acrylic acid is being distilled off.

10. A process as claimed in claim 1, wherein the precipitation of the copper sulfide is effected after completion or partial neutralization of the product obtained after the excess (meth)acrylic acid has been distilled off.

* * * * *